United States Patent [19]

Vogt et al.

[11] 3,966,803

[45] June 29, 1976

[54] PROCESS FOR THE MANUFACTURE OF ALKALI METAL SALTS OF AMINO POLYCARBOXYLIC ACIDS

[75] Inventors: Wilhelm Vogt, Knapsack near Cologne; Hubert Neumaier, Hermulheim near Cologne; Erich Schallus, Cologne-Klettenberg; Günter Peantek, Hermulheim near Cologne, all of Germany

[73] Assignee: Hoechst Aktiengesellschaft, Frankfurt am Main, Germany

[22] Filed: Apr. 25, 1975

[21] Appl. No.: 571,771

Related U.S. Application Data

[63] Continuation of Ser. No. 333,006, Feb. 16, 1973, abandoned, which is a continuation of Ser. No. 791,139, Jan. 14, 1969, abandoned.

[30] Foreign Application Priority Data
Feb. 2, 1968 Germany............................ 1668927

[52] U.S. Cl............................................. 260/534 E
[51] Int. Cl.$^2$......................................... C07C 99/10
[58] Field of Search ............................... 260/534 E

[56] References Cited

UNITED STATES PATENTS

| | | | |
|---|---|---|---|
| 2,388,189 | 10/1945 | Schweitzer...................... | 260/534 E |
| 3,061,628 | 10/1962 | Singer et al...................... | 260/534 E |
| 3,183,262 | 5/1965 | Singer et al...................... | 260/534 E |
| 3,409,666 | 11/1968 | Foreman .......................... | 260/534 E |
| 3,463,811 | 8/1969 | Godfrey et al. ................. | 260/534 E |
| 3,463,812 | 8/1969 | Thunberg et al................ | 260/534 E |
| 3,772,374 | 11/1973 | Shen................................. | 260/534 E |

*Primary Examiner*—Joseph E. Evans
*Attorney, Agent, or Firm*—Connolly and Hutz

[57] ABSTRACT

Production of alkali metal salts of amino polycarboxylic acids by reaction of a suitable carboxylic acid nitrile with aqueous alkali at elevated temperature. The salts are produced from an amino polycarboxylic acid nitrile suspension in an aqueous alkali metal hydroxide solution, which has a minimum strength of substantially 30 % by weight and contains at least stoichiometric proportions of alkali metal hydroxide; the suspension is introduced into a reactor heated to a temperature between 60° and 150° C, and salt formation is effected by thorough agitation.

6 Claims, No Drawings

PROCESS FOR THE MANUFACTURE OF ALKALI METAL SALTS OF AMINO POLYCARBOXYLIC ACIDS

This application is a continuation of application Ser. No. 333,006, filed Feb. 16, 1973, and now abandoned, which is a continuation of application Ser. No. 791,139, filed Jan. 14, 1969 and now abandoned.

The present invention relates to a process for the manufacture of alkali metal salts of amino polycarboxylic acids, e.g. nitrilo triacetic acid or ethylene diamine tetracetic acid or the like, by treatment of a suitable nitrile with at least the stoichiometric proportion of alkali, at elevated temperature.

German Patent 1,197,092 describes a one-step process for the manufacture of trialkali metal salts of nitrilo triacetic acid, which comprises adding an aqueous mixture consisting of hydrogen cyanide and formaldehyde, stabilized by means of mineral acid, to an aqueous solution of an alkali metal hydroxide and ammonia, with careful temperature control. The reaction which occurs can be represented by the following equation:

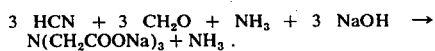

The stabilized mixture of hydrogen cyanide and formaldehyde is added to the aqueous solution of alkali metal hydroxide and ammonia within a period of time between 2 and 4 hours, the solution being initially maintained at a temperature between −5° and +5 C, which is gradually increased to substantially 100° C, as the reaction proceeds. In order to obviate undesirable coloration of the reaction product, it has been suggested that the hydrogen cyanide be used in an excess proportion, with respect to formaldehyde. Despite this, it has been found necessary to subject the resulting process product to separate purification to decolorize it, the purification comprising treating the product first with hydrogen peroxide of 35 % strength and later with active carbon. In view of the fact that the above process is carried out in a one-step-operation, it is clear that the resulting final product will be contaminated by undesirable by-products which are being formed upon the reaction of hydrogen cyanide, formaldehyde and ammonia. This is a further disadvantage accompanying the process.

A further process for the manufacture of trialkali metal salts of nitrilo triacetic acid has been described in U.S. Pat. No. 3,183,262. This process comprises reacting nitrilo triacetonitrile with a stoichiometric proportion of sodium hydroxide in an aqueous solution of the sodium salt of nitrilo triacetic acid, the solution always having between about 15 and 20 % free sodium hydroxide therein. The salt which precipitates from the alkaline solution on hydrolyzing it, is separated and washed by means of a saturated, aqueous solution of the sodium salt of nitrilo triacetic acid, until free from alkali. The mother liquids, which are obtained on making the salt and on effecting the washing step, respectively, are used for the preparation of further batches. It is necessary continuously to provide for the presence of an alkaline medium in the reaction mixture in order to effect precipitation of the nitrilo triacetic acid sodium salt from the aqueous phase. The above process admittedly enables the production of a relatively pure, crystalline salt, however, at the price of complicated multiple step purification. The process also calls for constant circulation of large quantities of mother liquid, which is disadvantageous.

A still further process for the production of trialkali metal salts of nitrilo triacetic acid has been described in BIOS-report 2326, which comprises reacting nitrilo triacetonitrile with a stoichiometric excess of sodium hydroxide in aqueous phase, at a temperature between 90° and 100° C. The resulting reaction solution is first treated with sodium hypochlorite and later with active carbon, to purify and decolorize it. The excess of alkali present in the reaction solution is finally neutralised by the introduction of $CO_2$, and the solution is spray-dried to produce the sodium salt of nitrilo triacetic acid with a purity of 85 to 92 %. Here again it is necessary to subject the resulting product to an additional purification step which impairs the economy of the process.

Althouth the saponification of amino polycarboxylic acid nitriles, for example nitrilo triacetonitrile with an alkali metal hydroxide, and the following salt formation are chemical processes that are relatively easy to carry out, the fact remains that it has not been possible heretofore to produce uncolored crude product which need not be purified separately.

In developing the process of the present invention, it has been found that the nitrilo groups of amino polycarboxylic acid nitriles, subjected to hydrolysis and salt formation by means of an alkali metal hydroxide, undergo condensation and produce brown coloration of the reaction product in all those cases in which under-stoichiometric proportions of alkali metal hydroxide appear anywhere in the saponification mixture. This means that the resulting colored product is required to be freed later from its contaminants by subjecting it to costly bleaching and absorptive treatment. No such purifying treatment is necessary in the process of the present invention.

The present process for the manufacture of alkali metal salts of amino polycarboxylic acids by reaction of a suitable carboxylic acid nitrile with aqueous alkali at elevated temperature comprises more particularly producing a reaction mixture by suspending the amino polycarboxylic acid nitrile in an aqueous alkali metal hydroxide solution, which has a minimum strength of substantially 30 % by weight and contains at least stoichiometric proportions of alkali metal hydroxide; introducing the resulting suspension into a reactor heated to a temperature between 60° and 150° C; inducing and effecting salt formation by thorough agitation, if desired, with the application of pressure, the suspension being introduced into the reactor at a rate sufficient for the inflating and vividly reacting reaction mixture to remain within a zone of thorough mixing; using substantially the reaction heat evolved for removing from the reactor ammonia in situ during the reaction and water present therein, the removal of the ammonia and water being effected continuously at a rate sufficient for all of the reaction mixture to remain moist with water or steam during the reaction; and evaporating resulting reaction product substantially to dryness.

It is particularly interesting to use the present process in those cases in which the starting material is nitrile triacetonitrile, ethylene diamine tetracetonitrile, stearyl amine-N-diacetonitrile or bis-(β-aminoethyl)-amine-N-pentacetonitrile, of which the resulting carboxylic acids or their alkali metal salts are known to be valuable technical products. Sodium hydroxide or potassium hydroxide, preferably in the form of about 30 to 50 weight percent aqueous solutions, are the preferred bases for making the alkali metal salts.

The viscosity of the starting mixture can be increased, if necessary or convenient, by the addition of the amino polycarboxylic acid-alkali metal salt to be produced, which is added in a proportion of up to 100 weight percent, referred to the nitrile quantity. Depending on the reaction conditions selected, the initially viscous solution will be found during the reaction to transform within a period between about 5 and 30 minutes, into a crystalline magma and finally into a dry, solid and white powder.

A further preferred variant of the present process comprises maintaining the reactor at a temperature between about 80° and 120° C, during the reaction. Temperatures higher than 120° C result in shorter reaction periods, however, at the price of more strongly colored products. Operation at temperatures maintained between about 80° and 120° C on the other hand results in the formation of uncolored products which need not be subjected to any separate purifying treatment. The temperature prevailing in the reactor can be readyly changed as desired by variation of the working pressure. The product obtained after completion of the reaction may be found to be contaminated with traces of ammonia. This can be removed by the introduction into the reactor, for example, of steam, air or inert gas, such as nitrogen or a similar gas. and washing of the reaction mixture, for a rather short time.

The reactors suitable for use in carrying out the process of the present invention include double Z-shaped kneaders, paddle mixers, ball mills, uniaxial or biaxial screw mixers and similar devices.

The alkali metal salts of nitrilo triacetic acid produced by the process of the present invention are obtained as a white powder which has been found to have the constitution of a monohydrate. The product obtained after completion of the reaction is practically dry and withstands storage, without caking. The product was analyzed to determine its nitrogen content and complex-forming properties; the process was found to result in the quantitative transformation of the amino polycarboxylic acid nitrile into the alkali metal salts of the carboxylic acid used.

This is a step forward in the art bearing in mind that the present process enables the one-step transformation with little expenditure of energy of amino polycarboxylic acid nitriles into alkali metal salts of suitable carboxylic acids, without the need to purify, decolorize or dry the resulting product, which is directly obtained in dry form.

EXAMPLE 1

A double Z-shaped kneader, whose heating jacket was maintained at a temperature of 95° C, was fed, within 15 minutes and with thorough agitation, with a mixture produced at room temperature from 402 grams or 3 mols nitrilo triacetonitrile (particle size <90 $\mu$) and 1200 grams or 9 mols sodium hydroxide solution of 30 % strength. The mixture was added at a rate sufficient for the foaming reaction mixture to remain within the zone of thorough mixing. After 20 minutes, there was obtained a substantially dry, colorless powder, which can be dried further in the kneader at elevated temperature, if desired. The powder was analyzed and found to contain 96.4 % trisodium salt of nitrilo triacetic acid ($Na_3NTE . H_2O$).

EXAMPLE 2

The procedure was the same as that described in Example 1 save that the starting mixture was used in combination with 136 grams or 0.5 mol trisodium salt of nitrilo triacetic acid, which was used in the form of its monohydrate ($Na_3NTE . H_2O$) and added to increase the viscosity of the starting mixture. The resulting colorless and after-dried powder was found to contain 99.5 % $Na_3NTE . H_2O$.

EXAMPLE 3

The procedure was the same as that described in Example 2 save that the temperature in the jacket of the double-Z-shaped kneader was increased to 120° C. The resulting, substantially colorless product was found to contain 97.4 % $Na_3NTE . H_2O$.

EXAMPLE 4

The procedure was the same as that described in Example 1 save that the starting mixture was used in further combination with 275 grams or 1 mol $Na_3NTE$, which was added to increase the viscosity of the starting mixture, and save that the nitrilo triacetonitrile had a particle size of up to 0.3 mm. The resulting colorless powder was found to contain 98 % $Na_3NTE . H_2O$.

EXAMPLE 5

The procedure was the same as that described in Example 1 save that 9.5 mols sodium hydroxide and 198.5 grams or 0.75 mol $Na_3NTE . H_2O$ had been used in the starting mixture, and save that the reaction was carried out at a temperature of 118° C in the heating jacket of the kneader. The resulting colorless product was found to contain 98 % $Na_3NTE . H_2O$.

EXAMPLE 6

A double Z-shaped kneader, whose heating jacket was maintained at a temperature of 120° C. was fed first with 600 grams or 4.5 mols sodium hydroxide solution of 30 % strength and fed later, with thorough agitation, with a mixture which had been produced at room temperature from 402 grams or 3 mols nitrilo triacetonitrile (particle size between 0.1 and 0.3 mm) and 600 grams sodium hydroxide solution of 30 % strength; the mixture was added in three portions to avoid excessive foaming of the reaction mixture. A slightly yellow-colored product was obtained, which was found to contain 95.8 % $Na_3NTE . H_2O$.

EXAMPLE 7

A double Z-shaped kneader, of which the heating jacket was maintained at a temperature of 85° C, was fed portionwise, within 17 minutes and with thorough agitation, with a mixture of 402 grams or 3 mols nitrilo triacetonitrile (particle size <90 $\mu$), 900 grams or 9 mole sodium hydroxide solution of 40 % strength, and 416 grams or 1.5 mols $Na_3NTE . H_2O$. After some 30 minutes, there was obtained an almost colorless product which was found to contain 96 % $Na_3NTE . H_2O$.

EXAMPLE 8

402 grams or 3 mols nitrilo triacetonitrile and 1260 grams or 9 mols potassium hydroxide solution of 40 % strength were mixed and the resulting mixture was introduced portionwise and with thorough agitation into a kneader, of which the heating jacket was maintained at 90° C. It took 15 minutes to produce quantitative saponification and salt formation. The viscous liquid obtained was found to transform into a crystalline solid only after about 2 hours.

EXAMPLE 9

A double Z-kneader, of which the heating jacket was maintained at a temperature of 95°C, was fed, within 45 minutes and with thorough agitation, with a mixture produced from 432 grams or 2 mols ethylene diamine tetracetonitrile and 1100 grams or 8.25 mols of sodium hydroxide solution having a strength of 30 % by weight. The mixture was added at a rate sufficient for the foaming reaction mixture to remain within the zone of thorough mixing. Prior to finishing the reaction, the reaction mixture was freed from traces of ammonia by rapid introduction of steam. After a total reaction period of 90 minutes, there was obtained a colorless dry powder which contained 98 % by weight tetrasodium ethylene diamine tetracetate.

We claim:

1. In the process for the production of alkali metal salts of an amino polycarboxylic acid selected from the group consisting of nitrilotriacetic acid and ethylene diamine tetraacetic acid by reacting an amino polycarboxylic acid nitrile selected from the group consisting of nitrilo triacetonitrile and ethylene diamine tetraacetonitrile with aqueous alkali at elevated temperatures, the improvement which consists essentially of suspending the amino polycarboxylic acid nitrile at room temperature in an aqueous alkali metal hydroxide solution which has a minimum strength of about 30% by weight and contains a stoichiometric proportion of alkali metal hydroxide, introducing the resulting suspension into a reaction zone heated to a reaction temperature of between 80° and 120°C., inducing and effecting salt formation by thorough agitation of the suspension in the reaction zone throughout the reaction, the suspension being introduced into the reaction zone at a rate sufficient for the foaming and rapidly reacting reaction mixture to remain within a zone of thorough mixing so that a stoichiometric proportion of alkali metal hydroxide is present in all portions of said mixing zone throughout the reaction, employing the heat evolved during the reaction to remove from the reactor the ammonia formed during the reaction and water present therein, the removal of the water and ammonia being effected continuously at a rate sufficient for the reaction mixture to remain moist with water or steam during the reaction, and evaporating the resulting moist reaction product substantially to dryness.

2. The process of claim 1, wherein the alkali metal hydroxide is a member selected from the group consisting of sodium hydroxide or potassium hydroxide.

3. The process of claim 1, wherein the alkali metal hydroxide is an alkali metal hydroxide solution of substantially 30 % by weight strength.

4. The process of claim 1, wherein the viscosity of the starting mixture is increased by the addition of the amino polycarboxylic acid-alkali metal salt to be produced, which is added in a proportion of up to 100 weight percent, referred to the nitrile.

5. The process of claim 1, wherein the reaction product is freed from traces of ammonia contained in it by short-time introduction into the reactor of a member selected from the group consisting of steam, air or an inert gas.

6. The process of claim 1, wherein the salt formation is effected under pressure.

* * * * *